United States Patent [19]

Moore, Jr.

[11] 4,315,856

[45] Feb. 16, 1982

[54] PROCESS FOR PREPARING 2,2-AZOBIS(2,4-DIMETHYLPENTANENI-TRILE)

[75] Inventor: Earl P. Moore, Jr., Hockessin, Del.

[73] Assignee: E. I. Du Pont de Nemours and Company, Wilmington, Del.

[21] Appl. No.: 117,987

[22] Filed: Feb. 4, 1980

[51] Int. Cl.³ ............................................. C07C 107/02
[52] U.S. Cl. .................................................... 260/192
[58] Field of Search ......................................... 260/192

[56] References Cited

U.S. PATENT DOCUMENTS

| | | | |
|---|---|---|---|
| 2,711,405 | 6/1955 | Anderson | 260/192 |
| 2,713,576 | 7/1955 | De Benneville | 260/192 |
| 3,775,395 | 11/1973 | Koyanagi et al. | 260/192 |
| 3,783,148 | 1/1974 | Fuchs | 260/192 |
| 3,876,622 | 4/1975 | Motokawa et al. | 260/192 X |
| 3,937,696 | 2/1976 | Knowles et al. | 260/192 |
| 3,987,025 | 10/1976 | Moore, Jr. | 260/192 |
| 4,028,345 | 6/1977 | Moore, Jr. | 260/192 |
| 4,039,527 | 8/1977 | Nagaoka et al. | 260/192 |
| 4,051,124 | 9/1977 | Moore, Jr. | 260/192 |
| 4,061,590 | 12/1977 | Moore, Jr. | 260/192 X |
| 4,132,729 | 1/1979 | Moore, Jr. | 260/465.5 |
| 4,218,371 | 8/1980 | Moore, Jr. | 260/192 |

Primary Examiner—Robert V. Hines

[57] ABSTRACT

A process for the preparation of 2,2'-azobis (2,4-dimethylpentanenitrile) with improved filtering and drying characteristics, said process comprising reacting 2-amino-2,4-dimethylpentanenitrile with a metal hypochlorite in the presence of water, a mixture of quaternary ammonium surface active compounds and ionic bromide wherein the equivalent ratio of ionic bromide to surface active compound is 0.4:1–12.0:1 at a temperature of about −10° C. to about 30° C., and recovering 2,2'-azobis(2,4-dimethylpentanenitrile) from the reaction mixture.

5 Claims, No Drawings

PROCESS FOR PREPARING 2,2'-AZOBIS(2,4-DIMETHYLPENTANENITRILE)

DESCRIPTION

1. Technical Field

This invention relates to an improved process for the preparation of 2,2'-azobis(2,4-dimethylpentanenitrile) from 2-amino-2,4-dimethylpentanenitrile, water, a metal hypochlorite and a mixture of surface active compounds. More specifically, this invention relates to a process for the preparation of 2,2'-azobis(2,4-dimethylpentanenitrile) with improved filtering and drying characteristics by reacting an aqueous hypochlorite solution with 2-amino-2,4-dimethylpentanenitrile in the presence of a mixture of surface active compounds and an ionic bromide.

2. Background Art

Azonitriles are produced by a process described by Anderson in U.S. Pat. No. 2,711,405 which involves reacting the cyanohydrin of an aliphatic ketone with ammonia to form an aminonitrile and oxidatively coupling the aminonitrile to form the azo using an alkali metal or alkaline earth metal hypochlorite in aqueous medium. De Benneville in U.S. Pat. No. 2,713,576 claimed essentially the same process with the addition of alkyl hypochlorites and restriction of aminonitriles to those of acetone, methyl ethyl ketone and diethyl ketone. A process improvement which enables azonitriles to be prepared from aminonitriles of higher molecular weight ketones in good yields is reported by Fuchs in U.S. Pat. No. 3,783,148. Methanol or ethanol is employed as a reaction solvent in proportion to the amounts of aminonitrile and hypochlorite solution used such that, at the completion of the reaction, the alcohol concentration is at least 70% by volume. The alcohol maintains a homogeneous system throughout the reaction and specifically prevents separation of the intermediate, highly hydrophobic chloramines.

U.S. Pat. No. 4,028,345 discloses a process which does not involve the alcohol solvent with all its drawbacks by coupling alpha-aminonitriles in the presence of a metal hypochlorite, water and a surface active compound to form aliphatic azodinitriles.

U.S. Pat. No. 4,051,124 discloses a process for preparing 2,2'-azobis(2-methylpropanenitrile) by coupling 2-amino-2-methyl-methylpropanenitrile in the presence of a metal hypochlorite, water and a mixture of a quaternary ammonium compound and a nonionic or amphoteric surface active compound. The 2,2'-azobis(2,4-dimethylpentanenitrile) produced by the aforesaid process has poor filtering and drying characteristics.

Disclosure of the Invention

Now it has been found that when 2,2'-azobis (2,4-dimethylpentanenitrile) is produced from 2-amino-2,4-dimethylpentanenitrile by reaction with a metal hypochlorite in the presence of water and a mixture of surface active compounds, the 2,2'-azobis(2,4-dimethylpentanenitrile) is isolated by filtration from the reaction mixture and dried much more rapidly when the surface active compounds are quaternary ammonium salts of particular chemical structures and there is also present ionic bromide. Accordingly, the process of the present invention comprises reacting 2-amino-2,4-dimethylpentanenitrile with a metal hypochlorite in an aqueous medium in the presence of a mixture of surface active quaternary ammonium salts and an ionic organic or ionic inorganic bromide compound in a concentration such that the equivalent ratio of ionic bromide ($Br^-$) to surface active compounds is from 0.4:1–12.0:1 at a temperature of about $-10°$ C. to about $30°$ C., the equivalent ratio of metal hypochlorite to aminoitrile being from 1.2:1–1.8:1 and separating the precipitated 2,2'-azobis(2,4-dimethylpentanenitrile) from the reaction mixture. This separation is rapidly done by filtration. The azodinitrile thus prepared possesses improved filtering and drying characteristics. The reaction mixture is preferably treated with $SO_2$ and a mineral acid sufficient to give a reaction mixture pH of from 2–5.5 before separation of the azodinitrile.

In the process of this invention, two molecules of the 2-amino-2,4-dimethylpentanenitrile are coupled to form the azodinitrile of the present invention. The coupling of the two molecules is accomplished in an aqueous medium with a metal hypochlorite and a mixture of surface active compounds comprising quaternary ammonium compounds. The aqueous medium also contains an ionic organic or ionic inorganic bromide either from the surface active compound or a separate compound.

By metal hypochlorite is meant a compound of the formula $M(OCl)_x$ where M is selected from the group consisting of sodium, potassium, calcium and mixtures thereof and x is the valence of M.

The preferred hypochlorite of the present invention, for reasons of convenience and economy, is sodium hypochlorite. Sodium hypochlorite can be prepared by passing chlorine gas into an aqueous sodium hydroxide solution at about $0°$ C. or it can be purchased commercially. Other hypochlorites can be prepared analogously. For the hypochlorite to be suitable for use in this invention, excess base is used to stabilize the hypochlorite solution. The base may be any water soluble base, preferably sodium or potassium hydroxide, but since sodium hydroxide is normally used in the commercial preparation of sodium hypochlorite, the most preferred base is sodium hydroxide and the amount of excess base must be at least 18 g/l, preferably 18–26 g/l and most preferably 22 g/l based one liter of 15% by weight metal hypochlorite. The excess base may, however, be added separately to the reaction mixture or to the hypochlorite. Poor yield or poor quality of the azonitrile will result or an oily product will be obtained if the excess base is not within the above limits. The base levels can be readily controlled by known manufacturing procedures.

The concentration of metal hypochlorite in the aqueous medium initially is from 5–10% by weight, preferably 5–8%. At hypochlorite concentrations below 5% product yields tend to drop off. Above about 10% hypochlorite concentration, colored product tends to form. A slurry solids content of 6.5% can be obtained with a 7% hypochlorite concentration. When the hypochlorite is calcium hypochlorite, the preferred concentration is reached by dilution with water. Calcium hypochlorite is available as a 100% active material. Sodium hypochlorite is commercially available as a 15% by weight aqueous solution.

The equivalent ratio of metal hypochlorite to the pentanenitrile is generally from 1.2:1–1.8:1. Ratios below 1.2:1 will not result in the improvements of higher yield and improved filterability or will not result in product formation. However, ratios above 1.8:1 do result in product formation, but offer no advantage. The aforesaid ratio of 1.2:1–1.8:1 results in high yields. The preferred ratio of the hypochlorite to the pentanenitrile is from 1.2:1–1.5:1. The most preferred ratio is 1.3:1. The equivalent ratio referred to herein is defined as the equivalent of metal hypochlorite per mole of aminonitrile. An equivalent of metal hypochlorite is a mole of the hypochlorite divided by the valence of the metal. An equivalent of aminonitrile is the same as the molar amount of aminonitrile.

The 2-amino-2,4-dimethylpentanenitrile starting material of the present invention can be obtained from commercial sources or may be prepared by methods well known in the art, for example, by the method described by Knowles in U.S. Pat. No. 3,541,132. A procedure that can be used to obtain the amino compound involves charging 4-methyl-2-pentanone to a platinum-lined pressure vessel and cooling this to 5° C. and then adding 1.0% of triethylamine based on the ketone weight. Hydrogen cyanide is then introduced in portions in an amount equimolar to that of the ketone at a temperature between 5° C. and 20° C. The reaction vessel is warmed to room temperature and pressurized to 40 psig with ammonia, heated to 50° C. and held at 50° C. and 80 psig for 8 hours and finally cooled and the product is discharged from the vessel.

The use of surface active compounds in the preparation of azodinitrile compounds is disclosed in U.S. Pat. Nos. 4,028,345 and 4,051,124. The disclosure in said U.S. patents is hereby incorporated by reference in the present application. While the function of the surface active compound in promoting this reaction is unknown, it may be as a "catalyst" for the reaction of base (e.g., NaOH) with intermediate formed chloramines and/or it may serve as a "solubilizer" for the chloramine and base, or it may perform some other function which enables a reaction to occur. The use of quaternary ammonium compounds and ionic bromide which may be a part of one or both of the quaternary ammonium compounds or a separate ionic inorganic or ionic organic bromide compound is a critical feature of the present invention. Although the function of the ionic bromide, Br$^-$, is not clearly understood, the reaction of Br$^-$ and hypochlorite is known to form hypobromite, which may act to more efficiently promote the formation of azodinitrile from the aminonitrile and influence the physical character of the azodinitrile such that superior filtration behavior and drying are obtained.

The quarternary ammonium compounds useful in this invention, their properties and behavior are discussed by Paul Becher in "Emulsions, Theory and Practice," ACS Monograph No. 162, 1965. Although the presence of the quaternary ammonium compounds of the present invention is critical, the amount may vary widely. As little as 0.75% by weight of quaternary ammonium compounds based upon the weight of the pentanenitrile can be used. As much as 3.0% can be used. No advantage is realized in using more than 3.0% and a tendency to produce a product with higher color may result at levels of about 3.0%. A preferred range of 1.0–1.75% by weight of quaternary ammonium compounds based on the aminonitrile gives desirable filtration properties. A most preferred level is 1.25%.

The quaternary ammonium compounds of this invention are specifically tetraalkylammonium compounds. A mixture of these compounds which fit two generic formulas is required. One compound of each type is required, although this does not preclude the use of more than one compound of each type as long as the condition is met that compounds which fit both generic formulas are employed and other requirements regarding their use is satisfied (specifically, the ratio of compounds of the two generic formulas as described below).

General formula A is

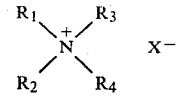

where $R_1$, $R_2$, $R_3$ and $R_4$ are alkyl groups with 1–18 carbon atoms, with one alkyl group having 10–18 carbon atoms and the remaining three alkyl groups having one or two carbon atoms. The preferred quaternary ammonium compounds are those with one alkyl group having 12–16 carbon atoms and three alkyl groups with one carbon atom. X is chloride, bromide, hydroxide, acetate, formate or any other anionic group which does not deleteriously affect the performance of the quaternary ammonium cation. The preferred groups are chloride, bromide, hydroxide, acetate and formate.

Representative examples of tetraalkylammonium salts of general formula A include:

Decyltriethylammonium bromide
Tetradecyltrimethylammonium acetate
Hexadecyltrimethylammonium chloride For economic and commercial availability reasons the tetraalkylammonium chloride compounds are preferred. Most preferred is hexadecyltrimethylammonium chloride.

General formula B is

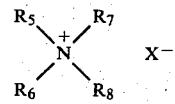

where $R_5$, $R_6$, $R_7$ and $R_8$ are alkyl groups with 1–14 carbon atoms, with at least two alkyl groups having 6–14 carbon atoms each. The total number of carbon atoms in $R_5+R_6+R_7+R_8$ ranges from 16–30. The preferred total number of carbon atoms is 18–26 and the preferred quaternary ammonium compounds are those with two alkyl groups of 7–12 carbon atoms each and two methyl groups. X is chloride, bromide, hydroxide, acetate, formate or any other anionic group which does not deleteriously affect the performance of the quaternary ammonium cation. The preferred groups are chloride, bromide, hydroxide, acetate and formate.

Representative examples of tetraalkylammonium salts of formula B include:

Dioctyldimethylammonium chloride
Didodecyldimethylammonium chloride
Hexyltetradecyldimethylammonium bromide
Dihexyldiethylammonium acetate
Trioctylmethylammonium bromide For economic and commercial availability reasons the tetraalkylammonium chloride compounds are preferred. Most preferred is dioctyldimethylammonium chloride.

The mole ratio of the compound selected from general formula A to the compound selected from general formula B can be as low as 0.5:1 and as high as 2.0:1 in order to obtain the benefits of the process of this invention. Use of a lower ratio tends to produce yellow or course azodinitriles while use of a higher ratio tends to give slower filtering azodinitriles. A preferred mole ratio of compound A and compound B is 0.61:1.

The sources of bromide ion ($Br^-$) in this invention may be either inorganic or organic. Thus, any water soluble salt of bromine may be used. These include NaBr, NBr, $CaBr_2$, LiBr, $MgBr_2$ and other inorganic bromides as well as organic amine hydrobromides such as trimethylamine hydrobromide and pyridine hydrobromide and quaternary ammonium bromides such as tetraethylammonium bromide and various surface active compounds containing the bromide ion that qualify as surface active compounds. Thus, one or more of the quaternary ammonium compounds which are used in the preparation of an azodinitrile can also serve as a total or partial source of bromide ion. That is, quaternary ammonium bromides can be employed. The process of the present invention involves the presence of certain ratios of ionic bromide to surfactants. The level of bromide used in conjunction with the surfactants to promote the formation of the azodinitrile compound from aminonitrile is best expressed in terms of an equivalent ratio of bromide ion to quaternary ammonium compounds. An equivalent ratio can be as low as 0.4:1 and as high as 12.0:1 in order to obtain the benefits of the process of this invention. Use of lower or higher ratios tends to produce course or yellow azodinitriles. A more preferable equivalent ratio of bromide ion to quaternary ammonium compound is 1.2:1–4.8:1. A most preferred ratio is 2.0:1.

The atmospheric pressure system is entirely aqueous, requiring no organic solvent to be present as a promoter or cosolvent with water in the preferred system. The quaternary ammonium surface active compounds and bromide are mixed with the water as is the sodium hypochlorite or other metal hypochlorite and the aminonitrile is added with sufficient cooling to handle the heat load. The manner in which the sodium hypochlorite and aminonitrile are combined is a matter of choice. The reactants can be added in separate streams to a body of water containing the surface active compound and bromide or the aminonitrile can be added to an aqueous metal hypochlorite solution containing the surfactant and bromide. In the present preferred system much higher azo solids slurries are possible than with the process of U.S. Pat. No. 3,783,148 enabling higher throughput with time and labor savings providing economic benefits. Thus, while product slurries with about 3% solids are obtained with the process of U.S. Pat. No. 3,783,148, the solids content of slurries of the present process is limited only by the upper useful limit of the hypochlorite concentration, which for this system, is about 10%.

The preferred temperature of the present process is 0°–10° C., but temperature may vary beyond our preferred temperature range in the process of the present invention. Desirable yields can be obtained at temperatures as high as 30° C. and as low as −10° C. The process of the present invention can be conducted at temperatures below −10° C. but at such lower temperatures, the danger of freezing of the aqueous mixture becomes greater and reaction times become longer. The use of antifreeze compounds may permit operation of the present process at temperatures lower than −10° C. without freezing. The process of the present invention can also be carried out at temperatures above 30° C. but at higher temperatures the risk of side reactions, azo decomposition and lower product yields, become a serious consideration. Thus, the process of the present invention may be conducted at a temperature that is above the freezing point of the reaction mixture and below the decomposition temperature of the azodinitrile compound.

The time required to complete the reaction of the present invention requires about 30 minutes at the preferred temperature.

Following completion of the reaction, the reaction mixture is a slurry of solid product partially in the form of very fine particles. It is desirable to treat the slurry with a chemical reducing agent in order to produce a product with good color and to eliminate odor causing impurities. Sulfur dioxide ($SO_2$) under acid conditions does an excellent job of effecting this, as described in U.S. Pat. No. 4,028,345. The use of $SO_2$ at a slurry pH of 2.0–5.5, adjusted with a mineral acid, is preferred at 0°–15° C. with a treatment time of about 30 minutes. The pH can then be increased to greater than 7.0 to prevent equipment corrosion during filtration. A suitable amount of $SO_2$ for this invention is about 0.12 lb per lb of aminonitrile reacted with hypochlorite.

The filter time is the time required to remove the liquid in the reaction product slurry leaving a wet cake of product. The wash time is the time required to wash out with water impurities in the wet cake and to remove said water to give a damp cake suitable for drying. The drying time is the time for the damp cake to be dried to constant weight at a set temperature under a constant regulated air flow.

The Examples below illustrate the importance of having both bromide ion ($Br^-$) and a mixture of surfactants of different structure in order to attain the benefits of this improved process.

EXAMPLE 1

(Single surfactant general formula A without $Br^-$)

Sixty grams of 2-amino-2,4-dimethylpentanenitrile (AN) of 90.5% purity were added in 50 minutes to a stirred mixture of 595 g 7% sodium hypochlorite solution containing 20 g of NaOH per liter of hypochlorite (15% basis) and 0.9 g hexadecyltrimethylammonium chloride (1.5% of AN weight) and the mixture maintained at 5° C. The equivalent ratio of NaOCl-to-AN was 1.3:1. The reaction mixture was stirred for 45 minutes longer at 5° C. and treated with 7.0 g $SO_2$ at a pH of 3.0 obtained by HCl addition. After completion of the $SO_2$ treatment, the reaction mixture was neutralized to pH 8.0 with NaOH and filtered. Filtration was conducted through 12.5 cm Whatman #41 paper on a Büchner funnel under 23 cm (9 in) Hg vacuum. The cake was washed with a volume of water equal to twice the volume of the reaction mixture. Times for filtration and washing were recorded as 4 minutes and 10 minutes, respectively. The cake was then pressed under full vacuum for 20 minutes and dried to constant weight at 40° C. under a controlled air flow. A drying time of 45 minutes was required. The dry product weighted 50.75 g, a 95.0% yield of 2,2'-azobis(2,4-dimethylpentanenitrile).

EXAMPLE 2

(Single surfactant general formula B without Br⁻)

Following the procedure of Example 1, 0.9 g dioctyldimethylammonium chloride was used in place of the hexadecyltrimethylammonium chloride. After 20 g of 2-amino-2,4-dimethylpentanenitrile had been added, a viscous yellow oil formed and the preparation was discontinued.

EXAMPLE 3

(Single surfactant general formula A with Br⁻)

Sixty grams of 2-amino-2,4-dimethyl-pentanenitrile (AN) of 91.2% purity were added in 50 minutes to 559 g 7% sodium hypochlorite solution containing 22 g of NaOH per liter of hypochlorite (15% basis) and 0.75 g hexadecyltrimethylammonium bromide (1.25% of AN weight) cooled at 5° C. The equivalent ratio of NaOCl-to-AN was 1.3:1. The equivalent ratio of Br⁻-to-quaternary ammonium compound was 1.0:1 since the surfactant itself furnished the Br⁻. The reaction mixture was stirred for 45 minutes at 5° C., treated with 7.0 g SO$_2$ at a pH of 3.0, neutralized to pH 9.0 with NaOH and filtered. Filtration, washing of the cake and drying as in Example 1 required 5.25 minutes, 10.3 minutes and 45 minutes, respectively. 51.5 Grams 2,2′-azobis(2,4-dimethylpentanenitrile) was obtained, a 95.6% yield.

EXAMPLE 4

(Single surfactant general formula B with Br⁻)

Following the procedure of Example 1, 1.05 g dioctyldimethylammonium chloride (1.75% of AN weight) was used in place of hexadecyltrimethylammonium chloride and, in addition, 0.7 g NaBr was included in the reaction mixture to give an equivalent ratio of Br⁻-to-quaternary ammonium salt of 2.10:1. After completion of the addition of the AN, a soft yellow solid formed and the preparation was discontinued.

BEST MODE

EXAMPLE 5

(Mixture of surfactants from general formulas A and B with Br⁻)

Sixty grams of 2-amino-2,4-dimethylpentanenitrile (AN) of 91.2% purity were added in 50 minutes to a stirred mixture of 600 g 7% sodium hypochlorite solution containing 22.3 g NaOH per liter of hypochlorite (15% basis), 0.288 g hexadecyltrimethylammonium chloride, 0.463 g dioctyldimethylammonium chloride and 0.5 g NaBr cooled at 5° C. The percent total surfactant was 1.25% of the AN weight, the equivalent ratio of Br⁻-to-quaternary ammonium compounds was 2.0:1, the mole ratio of hexadecyltrimethylammonium chloride-to-dioctyldimethylammonium chloride was 0.61:1 and the equivalent ratio of NaOCl-to-AN was 1.3:1. The reaction mixture was stirred for 30 minutes longer at 5° C., treated with 7.0 g SO$_2$ at a pH of 3.0, neutralized to pH 8.0 and filtered. The cake was washed and dried. Filtering, washing and drying steps were conducted as described in Example 1.

Filter Time: 1 min 24 sec
Wash Time: 2 min 54 sec
Drying Time: 20 min

Filtering and washing, therefore, were severalfold faster than in the previous Examples and drying time was reduced by half.

The yield of dry product was 51.6 g, a 96.9% yield.

EXAMPLE 6

(Mixture of surfactants from general formulas A and B without Br⁻)

The recipe and procedure of Example 5 were employed except no NaBr was included. The product obtained in 93% yield was a yellow solid of unacceptable quality.

EXAMPLES 7–8

Following the procedure of Example 5, 2,2′-azobis(2,4-dimethylpentanenitrile) is prepared by substituting the same total amount of the following surfactants for hexadecyltrimethylammonium chloride and dioctyldimethylammonium chloride in the molar ratios denoted with an equivalent ratio of Br⁻-to-surfactants of 2.0:

| Ex. | Quaternary Compounds | Mole Ratio A:B |
|---|---|---|
| 7 | Tetradecyltrimethyl-ammonium Acetate A Didodecyldimethyl-ammonium Chloride B | 0.55 |
| 8 | Dodecyltriethyl-ammonium Chloride A Hexyltetradecyldimethyl ammonium Chloride B | 1.75 |

| Ex. | Approx. Yield Azonitrile (%) | Filter Time | Wash Time | Dry Time |
|---|---|---|---|---|
| 7 | 95.6 | 1 min 30 sec | 3 min 30 sec | 25 min |
| 8 | 96.0 | 3 min | 6 min 20 sec | 35 min |

EXAMPLES 9–11

Following the procedure of Example 5, 2,2′-azobis(2,4-dimethylpentanenitrile) is prepared by varying the equivalent ratio of Br⁻-to-quaternary ammonium compounds using NaBr as the source of Br⁻ and the amount of surfactants:

| Ex. | Surfactant Conc. as % of Aminonitrile Wt. | Equiv. Ratio Br⁻:Quaternary Compounds |
|---|---|---|
| 9 | 1.0 | 10.0 |
| 10 | 1.75 | 4.0 |
| 11 | 2.5 | 0.6 |

| Ex. | Approx. Yield Azonitrile (%) | Filter Time | Wash Time | Dry Time |
|---|---|---|---|---|
| 9 | 93.5 | 2 min | 4 min 20 sec | 27 min |
| 10 | 94.5 | 1 min 50 sec | 5 min | 26 min |
| 11 | 94.0 | 3 min 10 sec | 4 min | 30 min |

EXAMPLES 12–13

2,2′-Azobis(2,4-dimethylpentanenitrile) is prepared according to the procedure of Example 5 except the following equivalent ratios of hypochlorite were used with the following bromide compounds to give an equivalent ratio of bromide-to-surfactants of 2.0:1.

| Ex. | Equiv. Ratio NaOCl:Surfactants | Bromide Compounds |
|---|---|---|
| 12 | 1.25 | LiBr |
| 13 | 1.5 | (CH$_3$)$_4$N$^+$ Br$^-$ |

| Ex. | Approx. Yield Azonitrile (%) | Filter Time | Wash Time | Dry Time |
|---|---|---|---|---|
| 12 | 96.5 | 1 min 50 sec | 3 min 25 sec | 25 min |
| 13 | 97.0 | 2 min 40 sec | 4 min | 25 min |

INDUSTRIAL APPLICABILITY

The azodinitrile compound produced by the process of the invention can be used as a polymerization initiator in emulsion dispersion and solution polymerization systems. Polymerization involving vinyl chloride, methyl methacrylate and butadiene-styrene are merely examples of such systems in industry that would benefit from the use of such initiators.

I claim:

1. A process for the preparation of 2,2'-azobis(2,4-dimethylpentanenitrile) comprising:
   (a) reacting at a temperature of from $-10°$ C. to 30° C.;
   (i) 2-amino-2,4-dimethylpentanenitrile;
   (ii) a 5 to 10% by weight aqueous metal hypochlorite solution having at least 18 g excess base per liter (15% basis);
   (iii) an ionic organic or inorganic bromide compound;
   (iv) at least 0.75% by weight based on the pentanenitrile of a mixture of quaternary ammonium compounds of formula A

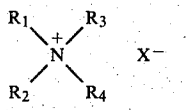

where $R_1$, $R_2$, $R_3$ and $R_4$ are alkyl groups with 1-18 carbon atoms, with one alkyl group having 10-18 carbon atoms and the remaining three alkyl groups having one or two carbon atoms; and formula B

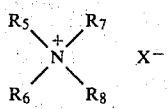

where $R_5$, $R_6$, $R_7$ and $R_8$ are alkyl groups with 1-14 carbon atoms, with at least two alkyl groups having 6-14 carbon atoms each with the total number of carbon atoms in $R_5+R_6+R_7+R_8$ from 16-30 and X in both formulas is chloride, bromide, hydroxide, acetate, formate or any other anionic group which does not deleteriously affect the performance of the quaternary ammonium cation, provided that if X in either formula is bromide the component (iii) need not be present; the equivalent ratio of (ii) to (i) being from 1.2:1 to 1.8:1, a bromide ion to (iv) equivalent ratio being from 0.4:1 to 12.0:1, and the mole ratio of the compound of formula A to that of formula B being from 0.5:1 to 2.0:1,
   (b) recovering the 2,2'-azobis(2,4-dimethylpentanenitrile) produced.

2. A process for the preparation of 2,2'-azobis(2,4-dimethylpentanenitrile) comprising:
   (a) reacting at a temperature of from $-10°$ C. to 30° C.;
   (i) 2-amino-2,4-dimethylpentanenitrile;
   (ii) a 5 to 8% by weight aqueous sodium, potassium, calcium or mixture thereof, hypochlorite solution having at least 18-26 g excess base per liter;
   (iii) an ionic organic or inorganic bromide compound;
   (iv) 0.75 to 3.0% by weight based on the pentanenitrile of a mixture of quaternary ammonium compounds of formula A

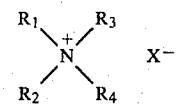

where $R_1$, $R_2$, $R_3$ and $R_4$ are alkyl groups with 1-18 carbon atoms, with one alkyl group having 10-18 carbon atoms and the remaining three alkyl groups having one or two carbon atoms; and formula B

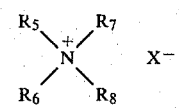

where $R_5$, $R_6$, $R_7$ and $R_8$ are alkyl groups with 1-14 carbon atoms, with at least two alkyl groups having 6-14 carbon atoms each with the total number of carbon atoms in $R_5+R_6+R_7+R_8$ from 16-30 and X in both formulas is chloride, bromide, hydroxide, acetate or formate, provided that if X in either formula is bromide the component (iii) need not be present; the equivalent ratio of (ii) to (i) being from 1.2:1 to 1.5:1; bromide ion to (iv) equivalent ratio being from 1.2:1-4.8:1, and the mole ratio of the compound of formula A to that of formula B being from 0.5:1 to 2.0:1;
   (b) recovering the 2,2'-azobis(2,4-dimethylpentanenitrile) produced.

3. A process for the preparation of 2,2'-azobis(2,4-dimethylpentanenitrile) comprising:
   (a) reacting at a temperature of from 0°-10° C.,
   (i) 2-amino-2,4-dimethylpentanenitrile;
   (ii) a 5 to 8% by weight aqueous sodium hypochlorite solution having at least 18-22 g sodium hydroxide per liter;
   (iii) an ionic organic or inorganic bromide compound;
   (iv) 1.0-1.75% by weight based on the pentanenitrile of a mixture of quaternary ammonium compounds of the formula A

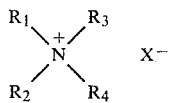

where $R_1$, $R_2$, $R_3$ and $R_4$ are alkyl groups with one alkyl group having 12–16 carbon atoms and the remaining three alkyl groups having one carbon atom; and formula B

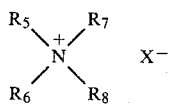

where $R_5$, $R_6$, $R_7$ and $R_8$ are alkyl groups with two alkyl groups having 7–12 carbon atoms and two methyl groups and X in both formulas is bromide provided that if X in either formula is bromide the component (iii) need not be present; the equivalent ratio of (ii) to (i) being from 1.2:1 to 1.3:1 and a bromide ion to (iv) being 2.0:1, and the mole ratio of the compound of formula A to that of formula B being 0.61:1;

(b) recovering the 2,2'-azobis(2,4-dimethylpentanenitrile) produced.

4. The process of claim 3 wherein the quaternary ammonium compounds are hexadecyltrimethylammonium chloride and dioctyldimethylammonium chloride.

5. The process of claim 3 wherein the amount of the mixture of quaternary ammonium compounds is 1.25% by weight of the pentanenitrile.

* * * * *